US012496382B2

(12) United States Patent
Spickermann et al.

(10) Patent No.: US 12,496,382 B2
(45) Date of Patent: Dec. 16, 2025

(54) APPARATUS FOR AN EXTRACORPOREAL BLOOD TREATMENT

(71) Applicant: Fresenius Medical Care Deutschland GmbH, Bad Homburg (DE)

(72) Inventors: Reiner Spickermann, Burghausen (DE); Carsten Mueller, Euerbach (DE); Pascal Kopperschmidt, Dittelbrunn (DE); Andreas Maierhofer, Schweinfurt (DE); Alfred Gagel, Litzendorf (DE); Gerhard Wiesen, Bad Homburg (DE); Liubov Smyslova, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 41 days.

(21) Appl. No.: 17/425,380

(22) PCT Filed: Jan. 24, 2020

(86) PCT No.: PCT/EP2020/051762

§ 371 (c)(1),
(2) Date: Jul. 23, 2021

(87) PCT Pub. No.: WO2020/152333

PCT Pub. Date: Jul. 30, 2020

(65) Prior Publication Data

US 2022/0096720 A1 Mar. 31, 2022

(30) Foreign Application Priority Data

Jan. 24, 2019 (DE) ..................... 10 2019 101 774.2

(51) Int. Cl.
*A61M 1/16* (2006.01)
*A61M 1/34* (2006.01)

(52) U.S. Cl.
CPC ........ *A61M 1/1656* (2013.01); *A61M 1/1603* (2014.02); *A61M 1/1611* (2014.02);
(Continued)

(58) Field of Classification Search
None
See application file for complete search history.

(56) References Cited

U.S. PATENT DOCUMENTS 4,508,622 A * 4/1985 Polaschegg ......... A61M 1/1609 210/321.71
4,601,830 A * 7/1986 Chen .................. A61M 1/1656 210/96.2
(Continued)

FOREIGN PATENT DOCUMENTS

DE 69733657 12/2005
DE 102015010417 A1 3/2017
(Continued)

OTHER PUBLICATIONS

Korean Office Action.
(Continued)

*Primary Examiner* — Krishnan S Menon
(74) *Attorney, Agent, or Firm* — Kilyk & Bowersox, P.L.L.C.

(57) ABSTRACT

The present invention relates to an apparatus for an extracorporeal blood treatment having an extracorporeal blood circuit in which a dialyzer is arranged and having a dialyzate circuit, wherein the blood circuit is in fluid communication with a first chamber and the dialyzate circuit is in fluid communication with a second chamber of the dialyzer, and wherein the two chambers are separated from one another by a semipermeable membrane, with a dialyzate pump for a conveying of the dialysis solution being present in the dialyzate circuit, wherein the apparatus has a control unit that is configured to operate the apparatus in a first phase and in a second phase following the first phase, wherein the dialyzate pump is operated with a smaller flow rate in the first phase than in the second phase and/or wherein the
(Continued)

dialyzate pump conveys a dialysis solution in the first phase that is of a higher concentration with respect to at least one component than in the second phase.

18 Claims, 1 Drawing Sheet

(52) U.S. Cl.
CPC .......... *A61M 1/3406* (2014.02); *A61M 1/341* (2014.02); *A61M 1/3413* (2013.01); *A61M 2205/3334* (2013.01); *A61M 2205/3379* (2013.01); *A61M 2230/20* (2013.01)

(56) References Cited

U.S. PATENT DOCUMENTS

| | | | | |
|---|---|---|---|---|
| 4,722,798 | A | 2/1988 | Goss | |
| 6,860,866 | B1 | 3/2005 | Graf et al. | |
| 9,402,941 | B2 | 8/2016 | Rambod et al. | |
| 2009/0221948 | A1* | 9/2009 | Szamosfalvi | A61M 1/3441 604/6.07 |
| 2010/0276367 | A1 | 11/2010 | Zhang | |
| 2013/0327713 | A1 | 12/2013 | Jirka et al. | |
| 2014/0190891 | A1* | 7/2014 | Lura | A61M 1/1605 210/85 |
| 2018/0236151 | A1 | 8/2018 | Kreuzberg et al. | |

FOREIGN PATENT DOCUMENTS

| | | | | |
|---|---|---|---|---|
| DE | 102016008755 | | 1/2018 | |
| EP | 0613688 | | 9/1994 | |
| EP | 0942759 | | 6/2005 | |
| EP | 1776972 | A1 | 4/2007 | |
| EP | 2421577 | B1 * | 10/2017 | A61M 1/16 |
| JP | 2-68069 | A | 3/1990 | |
| JP | 2001029456 | A | 2/2001 | |
| JP | 2011509131 | A | 3/2011 | |
| JP | 2011110349 | A | 6/2011 | |
| NL | 2018577 | A | 8/2018 | |
| WO | 2004022135 | A1 | 3/2004 | |
| WO | WO-2010121805 | A1 * | 10/2010 | A61M 1/16 |

OTHER PUBLICATIONS

Chinese Office Action.

Office Action issued in corresponding Brazilian Patent Application BR112021014242-8 dated Sep. 18, 2025 (8 pages).

Dialysis machine, Instructions for use, Dialog Iq, Sw 1.02.xx DE, Dec. 2017 (22 pages).

Meyer, Gunther, "Acute and Chronic Hemodialysis: Device," Pabst Science Publishers, 1999 (12 pages).

Thijssen et al., "The Evils of Intradialytic Sodium Loading," Vascular Access and Dry Weight, 2011, vol. 171, pp. 84-91.

Werner, Jurgen, "Cooperative and Autonomous Systems in Medical Technology: Functional Restoration," Sep. 1, 2014 (6 pages).

* cited by examiner

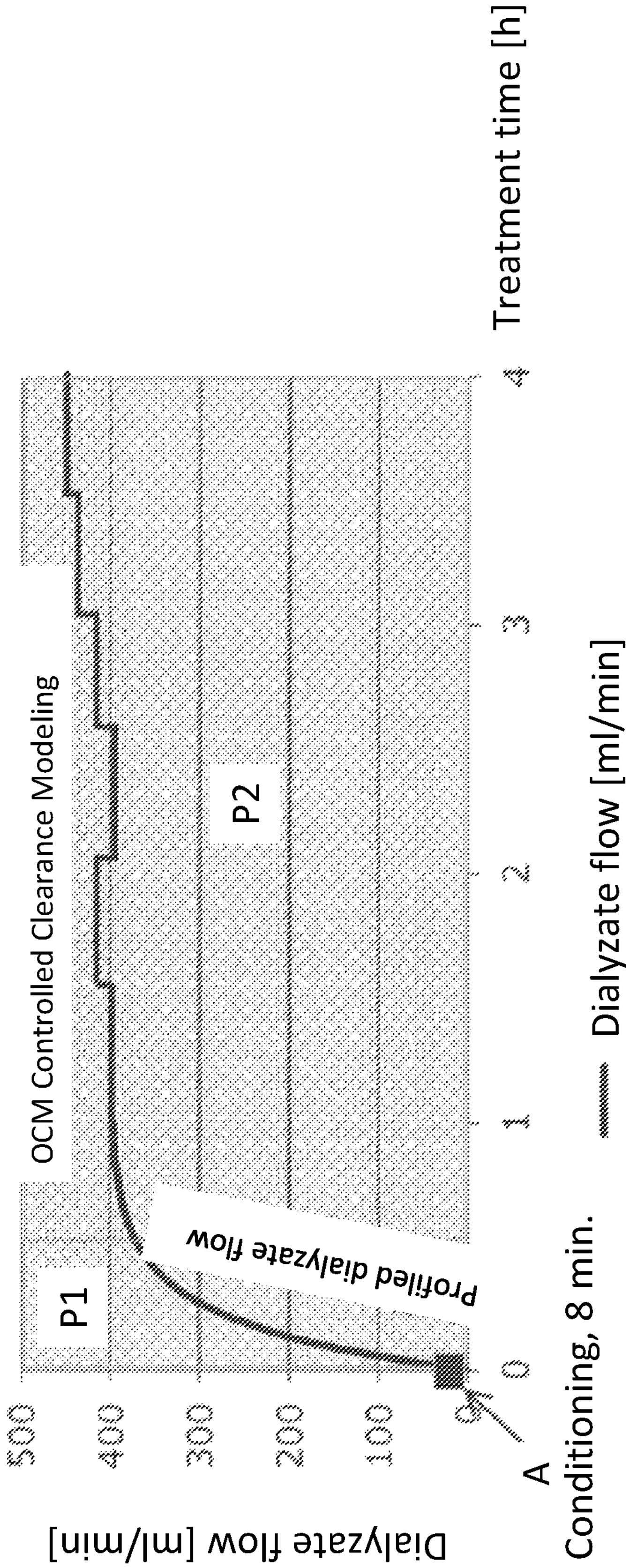
OCM Controlled Clearance Modeling
P1
P2
Profiled dialyzate flow
Dialyzate flow [ml/min]
500
400
300
200
100
0
0
1
2
3
4
Treatment time [h]
A
Conditioning, 8 min.
Dialyzate flow [ml/min]

APPARATUS FOR AN EXTRACORPOREAL BLOOD TREATMENT

The present invention relates to an apparatus for an extracorporeal blood treatment having an extracorporeal blood circuit in which a dialyzer is arranged and having a dialyzate circuit, wherein the blood circuit is in fluid communication with a first chamber and the dialyzate circuit is in fluid communication with a second chamber of the dialyzer, and wherein the two chambers are separated from one another by a semipermeable membrane, with a dialyzate pump for a conveying of the dialysis solution being present in the dialyzate circuit.

Such apparatus serve the removal of substances from the blood of the patient usually excreted in the urine that enter into the dialysis solution via the membrane of the dialyzer and that are in this manner removed from the blood of the patient.

An apparatus for an extracorporeal blood treatment having an extracorporeal blood circuit is known from EP 0 942 759 B1. Provision is made in the apparatus known from this document to approximate the actual dialysis efficiency (K/V) to a value for the maximum dialysis efficiency (K/V) max still tolerable for the patient during the treatment, i.e. to operate the treatment from the very start with an efficiency that is as high as possible to keep the treatment time as short as possible. The treatment is ended when the prescribed dialysis dosage (K t/V) has been reached, where t is the treatment time, K is the clearance, and V is the distribution volume of the patient.

During dialysis, complications can occur due to the transfer of electrolytes or other substances such as potassium ions or urea from the blood into the dialysis solution and said complications can result in complaints such as headaches, vomiting, etc., which is also known as disequilibrium syndrome.

It is the underlying object of the present invention to further develop an apparatus of the initially named kind such that the likelihood of occurrence of such complications and/or the gravity of the complications is reduced with respect to known machines.

This object is achieved by an apparatus for an extracorporeal blood treatment having an extracorporeal blood circuit in which a dialyzer is arranged and having a dialyzate circuit, wherein the blood circuit is in fluid communication with a first chamber and the dialyzate circuit is in fluid communication with a second chamber of the dialyzer, and wherein the two chambers are separated from one another by a semipermeable membrane, with a dialyzate pump for a conveying of the dialysis solution being present in the dialyzate circuit, characterized in that the apparatus has a control unit that is configured to operate the apparatus in a first phase and in a second phase following the first phase, wherein the dialyzate pump is operated with a smaller flow rate in the first phase than in the second phase and/or wherein the dialyzate pump conveys a dialysis solution in the first phase that is of a higher concentration with respect to at least one component than in the second phase.

Provision is accordingly made that the apparatus has a control unit that is configured to operate the apparatus in a first phase and in a second phase following the first phase, wherein the dialyzate pump is operated with a smaller flow rate in the first phase than in the second phase and/or wherein the dialyzate pump conveys a dialysis solution in the first phase that is of a higher concentration with respect to at least one component than in the second phase.

The second phase is preferably immediately subsequent to the first phase. However, the case is also covered by the invention that the second phase starts spaced apart in time from the end of the first phase.

It is thus the underlying idea of the present invention to select the dialysis flow at the start of the treatment as lower than at a later point in time or to use a dialysis solution at the start of the treatment that is of a higher concentration with respect to one or more substances than at a later point in time of the treatment. This substance or these substances are preferably those that are also present in the blood such as sodium ions, etc.

It is achieved by both measures that the withdrawal of substances from the blood that are usually excreted in the urine takes place comparatively slowly at the start of the treatment, which results in increased compatibility of the treatment for the patient and which considerably reduces the likelihood of the occurrence of disequilibrium syndrome or the severity of the symptoms. The prescribed flow rate or concentration of the dialysis solution is thus not reached or set from the start, but rather only at a later point in time of the treatment, e.g. after 30 min.

If a correspondingly lower dialyzate flow is set in the first phase, a correspondingly slower diffusive transfer of substance from the blood into the dialysis solution takes place. The same applies accordingly when the concentration of a component also found in the blood and to be depleted therein is initially set as high in the dialysis solution so that the concentration gradient between the blood and the dialysis solution is small, which likewise results in an initially low diffusion rate from the blood.

The control unit can be configured such that the flow rate and/or the concentration is constant or varies in the first phase and/or in the second phase, with the variation preferably taking place linearly, exponentially, or step-wise. In principle, any desired profiling of the flow rate and/or of the concentration is covered by the invention.

It is conceivable that a profiling of the flow rate and/or of the concentration of at least one substance of the dialysis solution takes place only in the first phase that is fixedly predefined or that is depending on one or more parameters and that a setting of the flow rate and/or of the concentration of at least one substance of the dialysis solution takes place in the second phase in accordance with different criteria than in the first phase, for example in dependence on measurement values such as the measured clearance.

The control unit can be designed such that the variation of the flow rate of the dialysis solution and/or of the concentration of the component(s) in question in the dialysis solution takes place only in the first phase, only in the second phase, or both in the first phase and in the second phase. It is conceivable that the dialysis machine is operated with a constant flow rate and/or concentration with respect to the dialysis solution in the first and/or second phases.

It is conceivable that the control unit is configured such that no variation of the flow rate of the dialysis solution and/or no variation of the concentration of the dialysis solution takes/take place in the second phase.

The control unit can be configured such that the first phase extends over a time span of 15 min. to 60 min., preferably over a time span of 20 min. to 40 min., and particularly preferably over a time period of 30 min.

The aforesaid values are naturally examples that do not restrict the invention.

The control unit can be configured such that a conditioning phase takes place prior to the first phase, e.g. for a duration of 5 min. to 10 min., in which no dialysis takes place, but only a hemofiltration. In this phase, that can represent the start of the treatment, there is thus only convective clearance due to a pressure drop over the membrane, but no diffusive clearance.

The first phase of the treatment then follows on directly or spaced apart in time from this conditioning phase. Such a conditioning phase is e.g. known from DE 10 2016 008 755 A1 whose disclosure content is herewith made the subject matter of the present invention.

The duration of the first phase can be constant for all the patients or can be dependent on one or more treatment parameters and/or patient parameters such as on body weight and/or on the distribution volume of the patient and/or on the substance concentration in the blood such as on the predialytic urea concentration. The duration of the second phase is preferably dependent on when the prescribed dialysis dosage is reached.

The control unit can be designed such that the flow rate and/or the concentration is set in the second phase in dependence on the clearance determined during the treatment or on the dialysis dosage reached during the treatment. Online clearance monitoring is thus conceivable, i.e. a clearance measurement taking place in real time and, dependent thereon, the setting of the flow rate and/or of the concentration of the dialysis solution.

It is also conceivable to set a specific profile for the setting of the flow rate and/or the concentration of the dialysis solution for the first and/or second phases before or at the start of the treatment, with said profile then being run through by the control unit and independently of any measurement values.

The transition from the first phase into the second phase can take place continuously or step-wise with respect to the concentration and/or with respect to the dialyzate flow. It is, for example, conceivable to set a specific first flow rate and/or concentration of the dialysis solution in the first phase and to set a second flow rate and/or concentration of the dialysis solution in the second phase or at least at its start or permanently so that a step-like transfer results.

However, a continuous transition from the first phase to the second phase with respect to the flow rate and/or the concentration of the dialysis solution is also covered by the invention.

The control unit can be configured to operate the apparatus as a hemodialysis machine or as a hemodiafiltration machine. In other words, the machine can be a hemodialysis machine or a hemodiafiltration machine. The case is also conceivable and is covered by the invention that the machine is operated as a simple hemofiltration machine at times, i.e. without dialysis solution being present in the dialyzer.

It is likewise conceivable that the machine has one or more lines for a substitution fluid that is added to the blood only upstream, only downstream, or both upstream and downstream of the dialyzer. The control unit can here be configured to set the flow of the substitution solution lower in the first phase than in the second phase. It is, for example, conceivable to allow the flow of substitution solution to increase from the value of zero at the start of the treatment to the prescribed value and/or to design the substitution rate as depending on the flow rate of the dialysis solution.

It is pointed out here that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Further details and advantages of the invention result from an embodiment shown in the drawing.

The only FIGURE shows the progression of the flow rate of the dialysis solution over time in an apparatus in accordance with the invention.

The flow rate of the dialysis solution flowing through the dialyzer is shown on the ordinate and the time on the abscissa.

As can be seen from the FIGURE, an increase of the flow rate of the dialysis solution through the dialyzer takes place in a first phase P1 after a conditioning phase (point A) in which no diffuse mass transfer, but only a convective mass transfer of blood via the membrane into the dialysis solution takes place, with the increase becoming smaller in the first phase as time passes.

The vertical line in the FIGURE marks the border between the first and second phases. In the second phase P2, the flow rate of the dialysis solution is higher than in the first phase and largely constant.

The transition of the progression of the flow rate from the first phase to the second takes place, as can be seen from the FIGURE, steadily and without steps.

In the first phase P1, the progression of the flow rate is profiled, with the profile being able to be fixedly predefined or being able to depend on one or more parameters such as on the condition of the patient, on the body weight of the patient, on his distribution volume, etc.

In the second phase P2, the setting of the flow rate of the dialysis solution takes place in dependence on the clearance K (OCM controlled clearance modeling) measured in the second phase and/or in dependence on the prescribed treatment time in which a specific dialysis dosage has to be reached or in accordance with a prescribed desired value or desired value profile.

As can be seen from the FIGURE, a fast removal of salts, urea, etc. is directly prevented at the start of the treatment due to the arising disequilibrium with its consequences associated therewith in that a comparatively small dialysis flow is set. The actually prescribed flow rate of the dialysis solution is therefore not reached by a ramping of the dialysate pump as fast as possible, but is rather reached with a deliberate time delay by a slow increase of the flow rate.

The reaching of the flow rate in the second phase can take place step-wise or continuously as can be seen from the FIGURE.

A slower withdrawal of substances usually excreted in the urine at the start of the treatment with respect to the later treatment can also be achieved in that a different dialysis solution is used at the start of the treatment than at a later time in the treatment. An initially low and then higher reduction of the concentration of the substances in question in the blood can also be achieved in this manner. It is conceivable with this procedure that different dialysis solutions are used that are stored in different bags, etc. or that the concentration of one or more ingredients is varied linearly or step-wise in one and the same reservoir of the dialysis solution.

The invention claimed is:

1. An apparatus for an extracorporeal blood treatment of a patient, said apparatus comprising:

an extracorporeal blood circuit including a dialyzer, a dialyzate circuit, a control unit, and an online clearance monitor configured to take clearance measurements in real time and to send measurement values of clearance to the control unit, wherein the dialyzer comprises a first chamber, a second chamber, and a semipermeable membrane, the extracorporeal blood circuit is in fluid communication with the first chamber of the dialyzer, the dialyzate circuit includes the second chamber of the dialyzer and further comprises a dialyzate pump that is in fluid communication with the second chamber of the dialyzer, and a dialyzate supply system comprising either (i) different dialysis solutions of different concentrations, stored in different bags, or (ii) a reservoir of dialysis solution and means to vary respective concentrations of one or more ingredients of the dialysis solution, the first chamber and the second chamber are separated from one another by the semipermeable membrane, the dialyzate pump is configured to convey a dialysis solution through the dialyzate circuit;

the control unit is configured to operate the apparatus in a first phase of hemodialysis and in a second phase of hemodialysis, the control unit is configured to set a duration of the first phase of hemodialysis based on one or more patient parameters including a concentration of at least one component, the at least one component being present at a concentration in the patient's blood, the control unit is configured to operate the dialyzate pump at a first flow rate during the first phase of hemodialysis, the control unit is configured to operate the apparatus in the second phase of hemodialysis following the first phase of hemodialysis, the control unit is configured to operate the dialyzate pump at a second flow rate during the second phase of hemodialysis, the control unit is configured to set a concentration of the at least one component, in the dialysis solution in the first phase, to be of a relatively higher first concentration, and the control unit is configured to control the dialyzate supply system to provide a concentration of the at least one component, in the dialysis solution in the second phase, to be of a second concentration that is relatively lower than the first concentration and that is set in dependence on the measurement values of clearance sent to the control unit from the online clearance monitor.

2. The apparatus in accordance with claim 1, wherein the control unit is configured to vary each of the first flow rate and the first concentration in the first phase and/or to vary each of the second flow rate and the second concentration in the second phase.

3. The apparatus in accordance with claim 2, wherein the control unit is configured to vary the first flow rate and the first concentration.

4. The apparatus in accordance with claim 1, wherein the control unit is configured such that no variation of the second flow rate and no variation of the second concentration, takes place in the second phase.

5. The apparatus in accordance with claim 1, wherein the control unit is configured such that the first phase extends over a time span of from 15 minutes to 60 minutes.

6. The apparatus in accordance with claim 1, wherein the control unit is further configured to operate the apparatus in a conditioning phase in which no dialysis takes place but hemofiltration takes place, before the first phase.

7. The apparatus in accordance with claim 1, wherein the control unit is configured such that the second concentration is set in the second phase in dependence on dialysis dosage (K t/V) reached during the treatment, where t is the treatment time, K is the clearance, and V is the distribution volume of the patient.

8. The apparatus in accordance with claim 1, wherein the control unit is configured such that the transition from the first phase into the second phase takes place continuously or step-wise with respect to setting the second concentration and/or with respect to setting the second flow rate.

9. The apparatus in accordance with claim 1, wherein the control unit is configured to operate the apparatus as a hemodialysis machine or as a hemodiafiltration machine, and optionally as a hemofiltration machine.

10. The apparatus in accordance with claim 1, wherein the control unit is configured such that the first phase extends over a time span of from 20 minutes to 40 minutes.

11. The apparatus in accordance with claim 1, wherein the control unit is configured such that the first phase extends over a time period of 30 minutes.

12. The apparatus in accordance with claim 1, wherein the control unit is configured such that each of the first flow rate and the first concentration is constant in the first phase.

13. The apparatus in accordance with claim 1, wherein the control unit is configured to maintain each of the first flow rate and the first concentration to be constant in the first phase and/or to maintain each of the second flow rate and the second concentration to be constant in the second phase.

14. The apparatus in accordance with claim 2, wherein the control unit is configured to vary the first flow rate and the first concentration in the first phase.

15. The apparatus in accordance with claim 2, wherein the control unit is configured to vary the second flow rate and the second concentration in the second phase.

16. The apparatus in accordance with claim 1, wherein the control unit is configured such that each of the first flow rate and the first concentration is varied in the first phase and the variation takes place linearly, exponentially, or step-wise.

17. The apparatus in accordance with claim 1, wherein the control unit is configured such that each of the second flow rate and the second concentration is constant in the second phase.

18. The apparatus in accordance with claim 1, wherein the control unit is configured such that each of the second flow rate and the second concentration is varied in the second phase and the variation takes place linearly, exponentially, or step-wise.

* * * * *